(12) United States Patent
Wang et al.

(10) Patent No.: US 7,454,296 B2
(45) Date of Patent: Nov. 18, 2008

(54) BIOSENSOR WITH MULTI-CHANNEL A/D CONVERSION AND A METHOD THEREOF

(76) Inventors: Kuo-Jeng Wang, 14, Kung-An St., Hsiao-Kang, Kaohsiung (TW); Chun-Jen Chen, 14, Lane 123, Hsin-I St., Wu-Chi Chen, Taichung (TW)

(*) Notice: Subject to any disclaimer, the term of this patent is extended or adjusted under 35 U.S.C. 154(b) by 976 days.

(21) Appl. No.: 10/722,549

(22) Filed: Nov. 28, 2003

(65) Prior Publication Data

US 2005/0000807 A1 Jan. 6, 2005

(30) Foreign Application Priority Data

Jul. 4, 2003 (TW) .............................. 92118314 A

(51) Int. Cl.
*G06F 3/02* (2006.01)

(52) U.S. Cl. ............................. 702/23; 702/22; 702/25; 702/30

(58) Field of Classification Search .............. 702/19, 702/23, 30, 32, 127, 179, 188, 22, 25; 204/403.01; 435/6; 600/347; 424/4, 9.2
See application file for complete search history.

(56) References Cited

U.S. PATENT DOCUMENTS 6,197,503 B1 * 3/2001 Vo-Dinh et al. ............... 435/6

6,349,230 B1 * 2/2002 Kawanaka ................. 600/347
6,407,395 B1 * 6/2002 Perov et al. .............. 250/458.1
7,232,510 B2 * 6/2007 Miyazaki et al. ....... 204/403.01

FOREIGN PATENT DOCUMENTS

CN 2528010 Y 12/2002

OTHER PUBLICATIONS

Zhang, Lin, & Sun, Guang; "12-Bit Data-Acquisition System MAX197 and its Application in the Harmonic Analyzer"; Electronic Engineer; May 1, 2002; pp. 37-42; vol. 28, issue 5; Jiangsu Province Scientific society; Nanjing, China.

* cited by examiner

*Primary Examiner*—Eliseo Ramos-Feliciano
*Assistant Examiner*—Felix Suarez
(74) *Attorney, Agent, or Firm*—Stolowitz Ford Cowger LLP

(57) ABSTRACT

A biosensor with multi-channel A/D conversion and a method thereof are provided. The present biosensor includes a chip generating a time-dependent analog signal in response to a content of a specific component of a specimen provided thereon, a multi-channel A/D converter, and a microprocessor. The multi-channel A/D converter has multiple channels simultaneously receiving the time-dependent analog signal in each sampling interval to convert the time-dependent analog signal to a set of digital signals. The microprocessor receives the sets of digital signals in a period of sampling time and determines the content of the specific component based on the sets of digital signals. The present biosensor provides a multi-channel A/D conversion for the time-dependent analog signal to improve the resolution of the determination of the content of the specific component.

20 Claims, 5 Drawing Sheets

BIOSENSOR WITH MULTI-CHANNEL A/D CONVERSION AND A METHOD THEREOF

BACKGROUND OF THE INVENTION

1. Field of the Invention

The present invention relates to a biosensor, and more particularly to a biosensor with multi-channel A/D conversion and a method thereof.

2. Description of the Prior Art

In recent years, various kinds of biosensors utilizing a specific catalytic action of enzymes to be used for clinical purposes have been developed. Most valuable use of such biosensors may be made in the area of e.g. diabetes treatment where it is vital for patients to keep their blood glucose concentration ("blood sugar level" below) within a normal range. For an inpatient, the blood sugar level can be kept normal under the supervision of the doctor. For an outpatient, self-control of the blood sugar level is an important factor for treatment in lack of doctor's direct supervision.

The self-control of the blood sugar level is achieved through a diet, exercise and medication. These treatments may often be simultaneously employed under the supervision of the doctor. It has been found that the self-control works more effectively when the patient himself is able to check whether or not his blood sugar level is within the normal range.

Recently, blood sugar determining instruments have been used for self-checking of blood sugar level. For example, U.S. Pat. No. 6,349,230 provides a blood sugar determining instrument, as shown in FIG. 1, which mainly includes a main detecting unit 10 and a chip 12 for blood sugar measurement. As shown in FIG. 2, the chip 12 includes a strip-like substrate 122 provided in its front portion with an electrode section 1221. The electrode section 1221 is covered by a reaction layer 124, a spacer 126 and a cover sheet 128. The electrode section 1221 is provided with an operational terminal 1222 and a counterpart terminal 1224 surrounding the operational terminal 1222. The operational terminal 1222 and the counterpart terminal 1224 are electrically connected to lead terminals 1226 and 1228, respectively, which are formed on a base end portion of the strip-like substrate 122. The reaction layer 124, which covers the electrode section 1221, contains potassium ferricyanide and an oxidase such as glucose oxidase.

The blood sugar determining instruments may be used in the following manner. A patient pricks his or her own skin with e.g. a lancet for oozing blood. Then, the oozed-out blood is caused to touch the tip of the chip 12 plugged into the main detecting unit 1. The blood is partially sucked into the reaction layer 124 by capillary action. The reaction layer 124 disposed above the electrode section 1221, is dissolved by the blood, which starts an enzyme reaction, as the following formula:

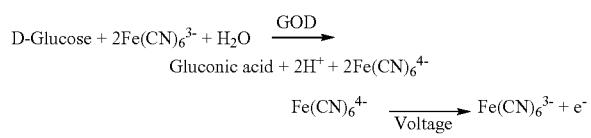

Potassium ferrocyanide is produced in an amount corresponding to the glucose concentration. After a certain period of time, a predetermined voltage $V_{ref}$ is applied on the chip 12 to electrochemically oxidize potassium ferrocyanide to release electrons. A response current is generated and passes through the operational terminal 1222. The response current is proportional to the concentration of potassium ferrocyanide produced by the enzyme reaction or to the concentration of the glucose. Therefore, the blood sugar level can be known by measuring the response current.

FIG. 3 is a schematic diagram of a control circuit of the blood sugar determining instrument of FIG. 1, in which the electrode section 1221 of the chip 12 can be regarded as a resistor $R_s$. The voltage $V_{ref}$ to be applied can be provided by a battery. The response current I generated by the chip 12 decays as time progresses to form a time-dependent discharge curve corresponding to the glucose concentration of the blood. Moreover, the response current I of each sampling time of the time-dependent discharge curve is converted to an output voltage $V_{out}$ by a current/voltage converter 30 formed of an operational amplifier 310 having an amplification resistance $R_f$. As a consequence, the response current I decaying as time progressing forms a voltage-time discharge curve, as shown in FIG. 4. Each voltage of each sampling time of the voltage-time discharge curve is converted to a set of digital signals by a single-channel A/D converter 32. A microprocessor 34 reads the digital signals output from the single-channel A/D converter 32, and calculates the glucose concentration of the blood in accordance with the digital signals. A reading of the glucose concentration is displayed on a display such as a liquid crystal display (LCD) 36.

The voltage-time discharge curve shown in FIG. 4 is sampled in each sampling interval, and then sent to the single-channel A/D converter to convert to a set of digital signals. However, the single-channel A/D converter has a limited resolution due to the design itself. As a result, the resolution of the detection of the conventional blood sugar instrument cannot be improved.

Accordingly, it is an intention to provide an improved biosensor, which can overcome the drawback of the conventional one.

SUMMARY OF THE INVENTION

It is one objective of the present invention to provide a biosensor with multi-channel A/D conversion, which is provided with an A/D converter with higher resolution to improve precision of the detection of a content of a specific component of a specimen provided on the present biosensor.

It is another objective of the present invention to provide a biosensor with multi-channel A/D conversion, which provides a multi-channel conversion for a time-dependent analog signal generated in response to a content of a specific component of a specimen detected by the present biosensor to improve the resolution of determination of the content of the specific component.

It is a further objective of the present invention to provide a biosensor with multi-channel A/D conversion, which can improve the resolution of the determination of a content of a specific component of a specimen without increasing complexity of the combination of elements of the present biosensor.

In order to achieve the above objectives of this invention, the present invention provides a biosensor with multi-channel A/D conversion and a method thereof. The present biosensor includes a chip generating a time-dependent analog signal in response to a content of a specific component of a specimen provided thereon, a multi-channel A/D converter and a microprocessor. The multi-channel A/D converter has multiple channels simultaneously receiving the time-dependent analog signal in each sampling interval in order that the multi-channel A/D converter converts the time-dependent analog signal to a set of digital signals. The microprocessor receives the sets of digital signals in a period of sampling time and determines the content of the specific component based on the sets of digital signals.

The present biosensor is provided with a multi-channel A/D converter, which outputs a set of digital signals with more bit number than a single-channel A/D converter used in the prior biosensor so as to improve the resolution of the A/D conversion. As a consequence, the precision of the detection of the present biosensor can be improved. Moreover, the present biosensor is readily provided since the complexity of the combination of the elements of the present biosensor is not increased upon adding the multi-channel A/D converter.

BRIEF DESCRIPTION OF THE DRAWINGS

The objectives and features of the present invention as well as advantages thereof will become apparent from the following detailed description, considered in conjunction with the accompanying drawings.

DESCRIPTION OF THE PREFERRED EMBODIMENTS

The present invention provides a biosensor with multi-channel A/D conversion and a method thereof. The present biosensor mainly includes a chip generating a time-dependent analog signal in response to a content of a specific component of a specimen provided thereon, a multi-channel A/D converter and a microprocessor. The multi-channel A/D converter has multiple channels simultaneously receiving the time-dependent analog signal in each sampling interval in order that the multi-channel A/D converter converts the time-dependent analog signal to a set of digital signals. The microprocessor receives the sets of digital signals in a period of sampling time and determines the content of the specific component based on the sets of digital signals. A reading of the content of the specific component can be displayed through a display. The present biosensor provides the multi-channel A/D conversion for the time-dependent analog signal sampled per sampling interval in order that the set of the digital signals converted therefrom with more bit number than that from a single-channel A/D converter used in the conventional biosensor. The multi-channel A/D converter of the present biosensor is able to increase the resolution of A/D conversion, and providing higher resolution than the single-channel A/D converter. Hence, the present biosensor can provide a precision of the detection to the content of the specific component of the specimen higher than that of the conventional one with the single-channel A/D converter.

Figure 1:
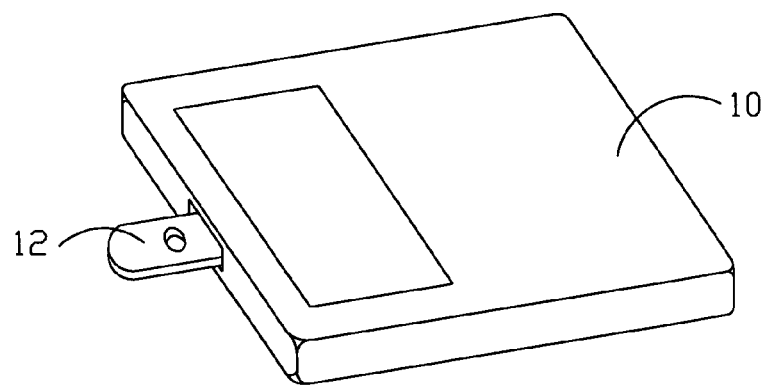
FIG. 1 is a schematic perspective view of a conventional blood sugar determining instrument.
Figure 2:
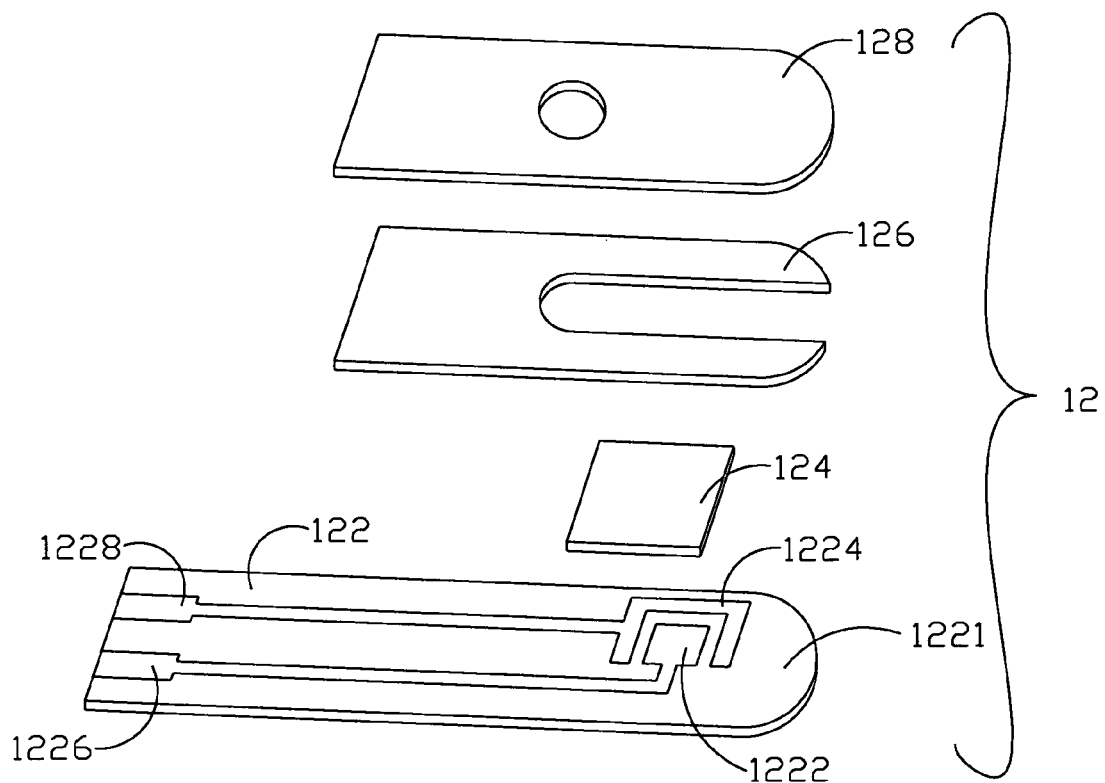
FIG. 2 is an exploded view of a chip of the conventional blood sugar determining instrument of FIG. 1.

The principle of the present biosensor for monitoring the content of the specific component of the specimen is the same with that of the conventional biosensor of FIG. 1. The specimen is applied on the chip having been plugged into the main detecting unit of the biosensor of the present invention. And, the content of the specific component to be detected present in the specimen is determined in accordance with a result of an enzyme-catalytic reaction between the specific component and the enzyme of the chip. Therefore, the specific component of the specimen to be detected depends on the type of the enzyme of the chip. For example, when the chip contains glucose oxidase, the biosensor can be used to monitor a glucose concentration of a blood sample. When the chip contains lactate oxidase, the biosensor can be used to monitor a concentration of lactic acid of saliva. For example, when monitoring the glucose concentration of the blood sample, the blood sample is applied on the chip of the present biosensor, the glucose of the blood sample and potassium ferricyanide proceed an electrochemical reaction under catalysis of the glucose oxidase, producing potassium ferrocyanide in an amount proportional to the glucose concentration. Hence, after a period of time that the blood sample has been applied on the chip, i.e. the enzyme-catalytic reaction completes, an applied voltage is applied on the chip in order for the chip generating a response current in response to the blood glucose concentration. That is, the applied voltage makes potassium ferrocyanide in the amount proportional to the glucose concentration proceeding oxidation to release electrons so as to generate the response current.

The present biosensor will be described and explained in detail in accordance with the following embodiments with reference to the drawings.

Figure 3:
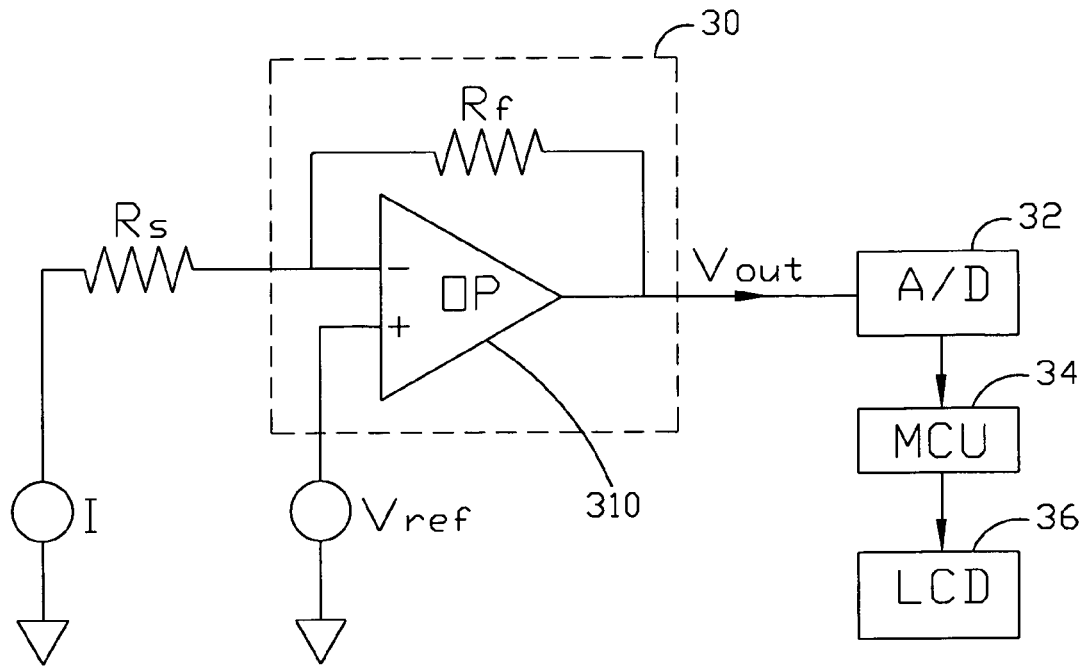
FIG. 3 is a schematic diagram of a control circuit of the conventional blood sugar determining instrument of FIG. 1.
Figure 4:
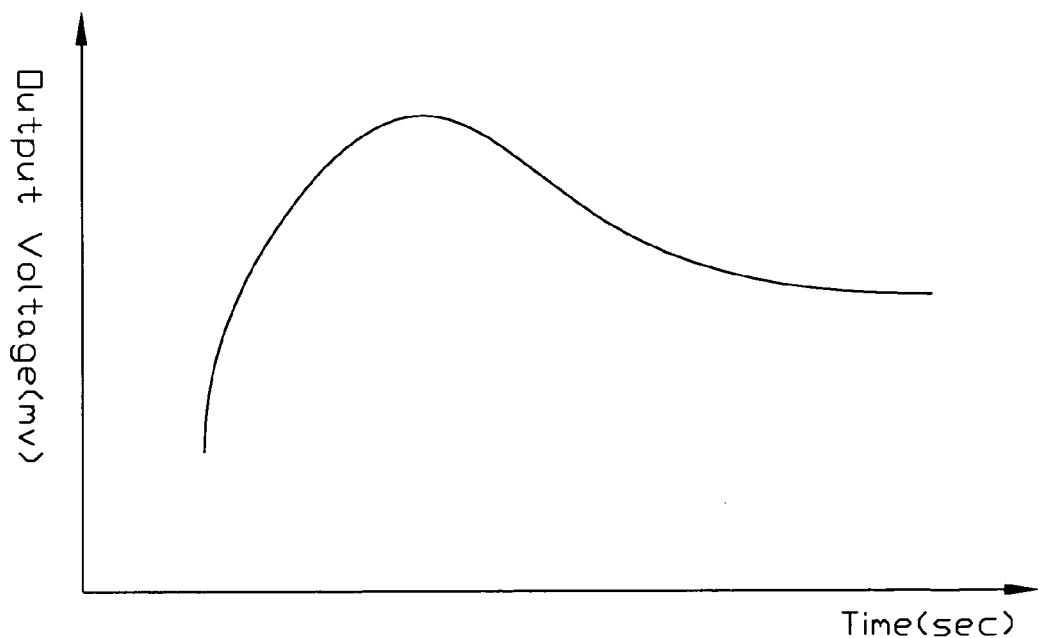
FIG. 4 is a diagram of a voltage-time discharge curve obtained from the conventional blood sugar instrument of FIG. 1.
Figure 5:
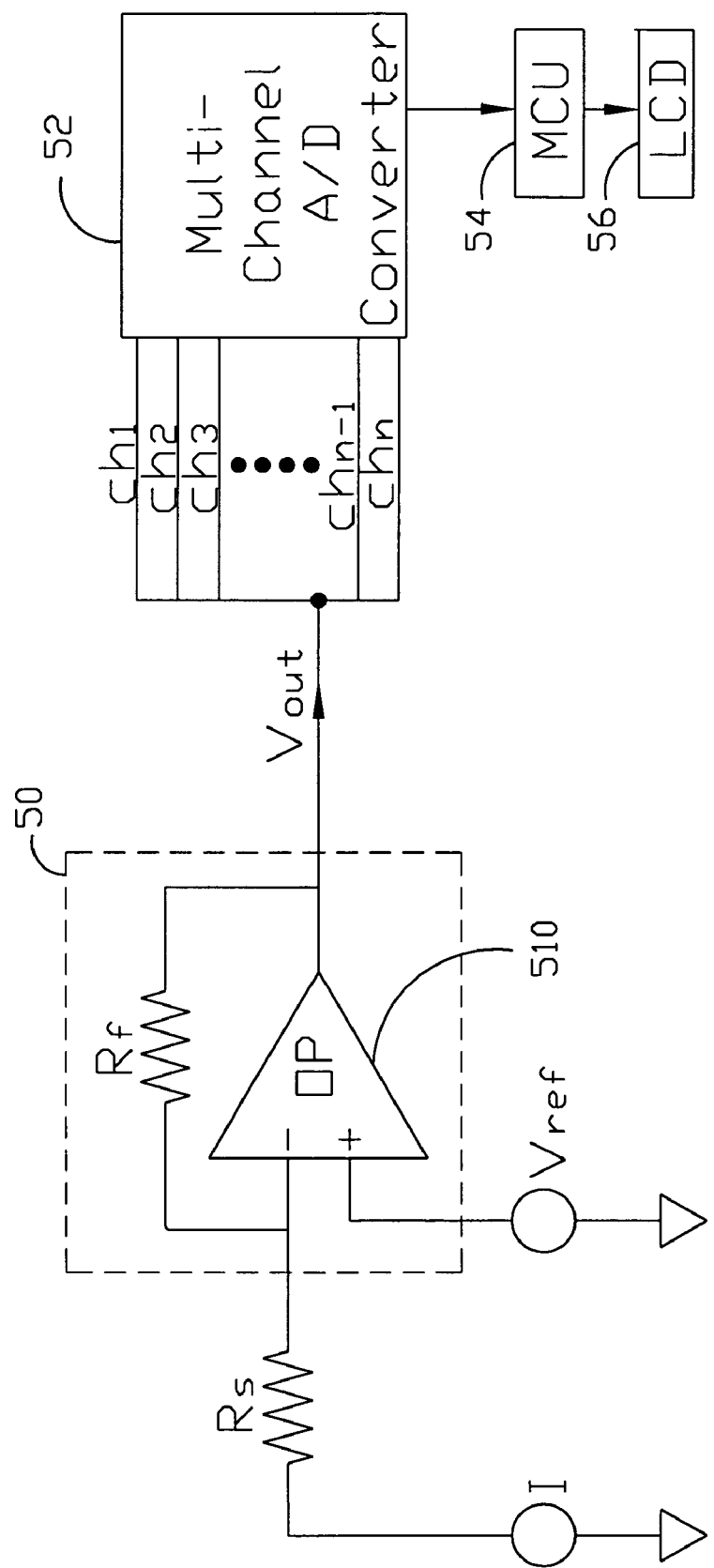
FIG. 5 is a schematic diagram of a control circuit of the present biosensor according to an embodiment.
Figure 6:
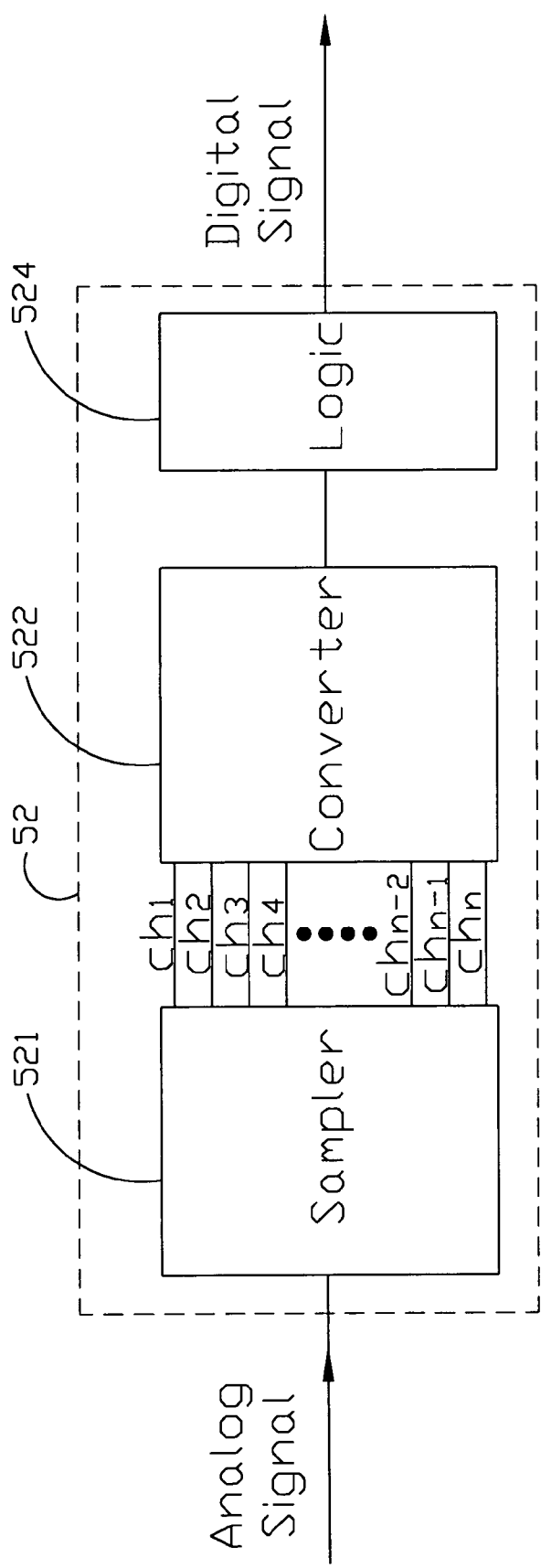
FIG. 6 is a schematic block diagram of a multi-channel A/D converter used in the present biosensor.

FIG. 5 is a schematic control circuit of the present biosensor according to one embodiment of the present invention. The present biosensor shown in FIG. 5 includes a chip having a resistance $R_s$ and a main detecting unit. The chip generates a time-dependent response current I passing through in response to a content of a specific component provided thereon upon an applied voltage applied on the chip. The main detecting unit includes a current/voltage converter 50, a multi-channel A/D converter (analog-to-digital converter) 52, a microprocessor 54 and a liquid crystal display 56. The current/voltage converter 50 including an operational amplifier 510 with an amplification resistance $R_f$ is used to convert the time-dependent response current I to a time-dependent voltage $V_{out}$. The time-dependent voltage $V_{out}$ is simultaneously sent to multiple channels $ch_1, ch_2, ch_3, \ldots, ch_{n-1}$ and $ch_n$ of the multi-channel A/D converter 52 to convert to a set of digital signals per sampling interval. Referring to FIG. 6, which is an exemplary block diagram of the multi-channel A/D converter 52. The multi-channel A/D converter 52 may include a sampler 521, a converter 522 having multiple channels and a logic circuit 524. The sampler 521 receives an analog signal per sampling interval, then sends the selected analog signal simultaneously to the multiple channels $ch_1$, $ch_2, ch_3, ch_4 \ldots, ch_{n-2}, ch_{n-1}$ and $ch_n$ of the converter 522 to convert to a number of sets of digital signals respectively corresponding to each of the multiple channels. The logic circuit 524 receives the sets of digital signals for combining them, and outputs a set of digital signals with more bit number than each of the sets of digital signals from the converter 522. For example, in case that a selected analog signal is inputted to each of the channel $ch_1, ch_2, ch_3, ch_4, \ldots, ch_{n-2}, ch_{n-1}$ and $ch_n$ of the converter 522 and converted to a set of 8-bit digital signals, respectively. The sets of 8-bit digital signals are sent to the logic circuit 524, and may be combined to a set of 10-bit digital signals, 12-bit digital signals, or 16-bit digital signals, based on the architecture of the logic circuit 524, for output. Hence, the multi-channel A/D converter 52 could have a resolution of A/D conversion higher than that of a single-channel A/D converter. Therefore, the present biosensor could have a resolution of detection higher than that of the conventional biosensor with the single-channel A/D converter 32, as shown in FIG. 3.

Referring to FIG. 5 again, the microprocessor 54 receives the sets of digital signals in a period of sampling time, and then determines the content of the specific component of the specimen in accordance with a time-dependent discharge curve constituted by the sets of digital signals. A peak value and a rising time corresponding thereto can be obtained from the time-dependent discharge curve. The peak value represents a maximum value of the time-dependent discharge curve. The microprocessor 54 can calculate the content of the specific component of the specimen by the following ways. First, a mapping table of peak value versus content of the specific component can be previously established in the microprocessor 54, and the microprocessor 54 determines the content of the specific component in accordance with the time-dependent discharge curve and the mapping table. Second, a mapping table of rising time versus content of the specific component can be previously established in the microprocessor 54, and the microprocessor 54 determines the content of the specific component in accordance with the time-dependent discharge curve and the mapping table. A reading of the content of the specific component of the specimen is displayed via a liquid crystal display 56.

Figure 7:
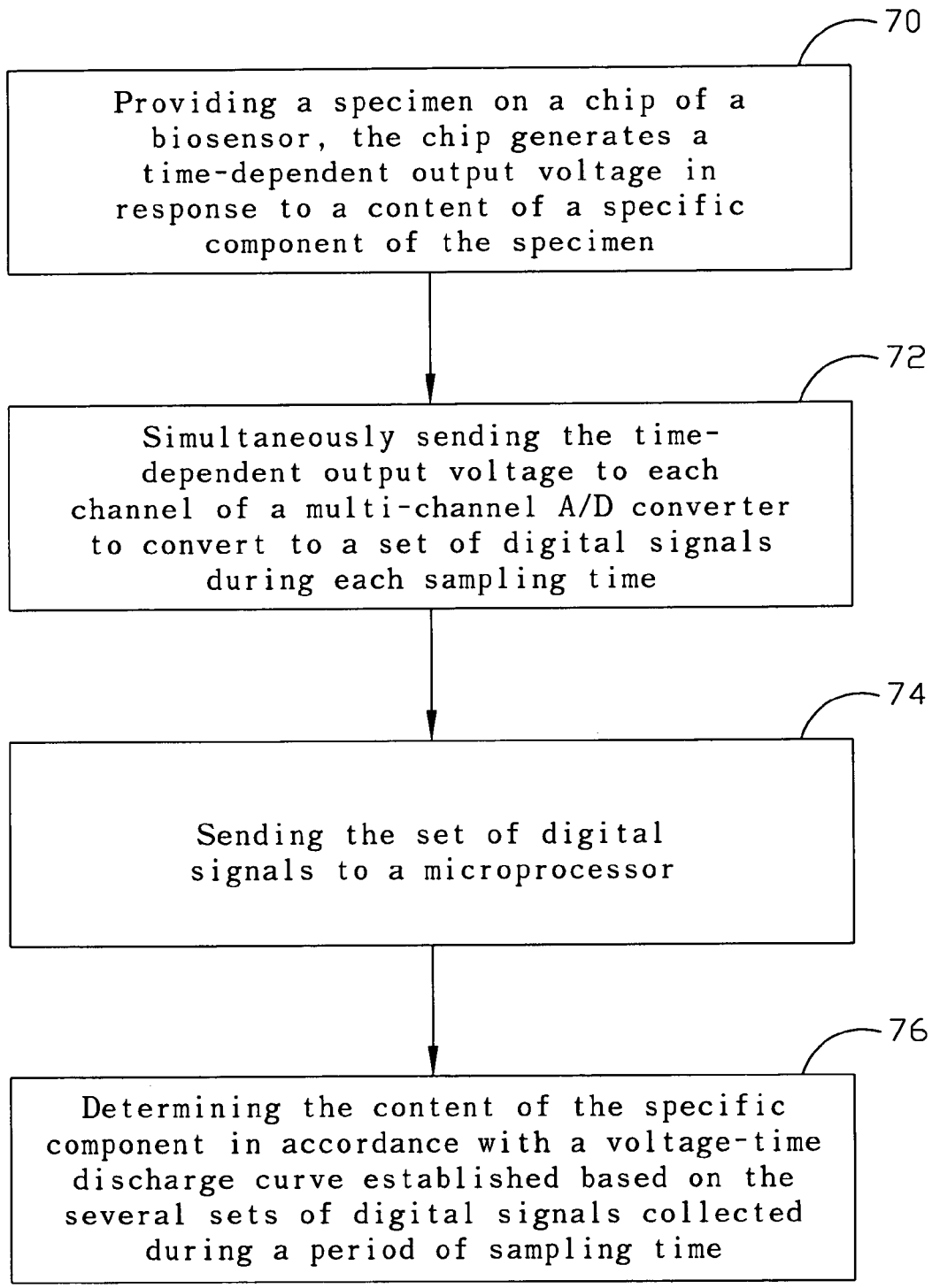
FIG. 7 is a flow chart of an example of the present method.

In another aspect of the present invention, the present invention provides a method for determining the content of the specific component of the specimen. FIG. 7 is a flow chart of an example of the present method, in step 70, the specimen is provided on the chip plugged into the main detecting unit of the present biosensor. The chip generates a time-dependent output voltage, in response to the content of the specific component of the specimen upon applying the applied voltage on the chip. In step 72, the time-dependent output voltage is simultaneously sent to each channel of the multi-channel A/D converter 52 to convert to a set of digital signals during each sampling time. Then, in step 74, the set of digital signals is sent to the microprocessor 54. In step 76, the microprocessor 54 determines the content of the specific component of the specimen in accordance with the time-dependent discharge curve constituted by the sets of digital signals collected during a period of sampling time. In addition, the microprocessor 54 calculates the content of the specific component of the specimen in accordance with the time-dependent discharge curve and the mapping table above-mentioned.

The present biosensor is provided with the multi-channel A/D converter, which outputs a set of digital signals with more bit number than a single-channel A/D converter used in the prior biosensor so as to improve the resolution of the A/D conversion. As a consequence, the precision of the detection of the present biosensor can be improved. The present biosensor is readily provided since the complexity of the combination of the elements of the present biosensor is not increased upon adding the multi-channel A/D converter.

The embodiments are only used to illustrate the present invention, not intended to limit the scope thereof. Many modifications of the embodiments can be made without departing from the spirit of the present invention.

What is claimed is:

1. A biosensor with multi-channel A/D conversion, comprising:
   a chip to generate a time-dependent analog signal in response to an enzyme reaction initiated by a specific component of a specimen making contact with the chip;
   a multi-channel A/D converter with multiple channels each of which is configured to simultaneously receive the time-dependent analog signal in each sampling interval, the multi-channel A/D converter being configured to convert the time-dependent analog signal to a set of digital signals; and
   a microprocessor to receive the set of digital signals in a sampling period and to determine the content of the specific component based on the set of digital signals.

2. The biosensor of claim 1, wherein the time-dependent analog signal includes a response current.

3. The biosensor of claim 2, further comprising a current/voltage converter to convert the time-dependent analog signal to a time dependent output voltage prior to sending to said multi-channel A/D converter.

4. The biosensor of claim 3, wherein said current/voltage converter includes an operational converter.

5. The biosensor of claim 1, wherein said multi-channel A/D converter includes a sampler, a multi-channel converter and a logic circuit.

6. The biosensor of claim 3, wherein said multi-channel A/D converter includes a sampler, a multi-channel converter and a logic circuit.

7. The biosensor of claim 4, wherein said multi-channel A/D converter includes a sampler, a multi-channel converter and a logic circuit.

8. The biosensor of claim 1,
   wherein said microprocessor includes a mapping table of peak value versus content of the specific component, the peak value representing a maximum value of a time-dependent discharge curve constituted by the sets of digital signals collected during the sampling period; and
   wherein said microprocessor is configured to determine the content of the specific component in accordance with the mapping table.

9. The biosensor of claim 3,
   wherein said microprocessor includes a mapping table of peak value versus content of the specific component, the peak value representing a maximum value of a time-dependent discharge curve constituted by the set of digital signals collected during the sampling period; and
   wherein said microprocessor is configured to determine the content of the specific component in accordance with the mapping table.

10. The biosensor of claim 1,
    wherein said microprocessor includes a mapping table of rising time versus content of the specific component, the rising time corresponding to a maximum value of a time-dependent discharge curve constituted by the set of digital signals collected during the sampling period; and
    wherein said microprocessor is configured to determine the content of the specific component in accordance with the mapping table.

11. The biosensor of claim 3,
    wherein said microprocessor includes a mapping table of rising time versus content of the specific component, the rising time corresponding to a maximum value of a time-dependent discharge curve constituted by the set of digital signals collected during the sampling period; and
    wherein said microprocessor is configured to determine the content of the specific component in accordance with the mapping table.

12. The biosensor of claim 1, wherein further comprising a liquid crystal display to display a reading of the content of the specific component.

13. The biosensor of claim 3, wherein further comprising a liquid crystal display to display a reading of the content of the specific component.

14. A method for determining a content of a specific component of a specimen, comprising:
   generating a time-dependent analog signal in response to a content of a specific component of the specimen initiating an enzyme reaction on a chip of a biosensor;
   simultaneously sending the time-dependent analog signal to each channel of a multi-channel A/D converter for converting to a set of digital signals during each sampling time;
   sending the set of digital signals to a microprocessor; and
   determining the content of the specific component in accordance with the set of digital signals collected during a sampling period.

15. The method of claim 14, wherein the time-dependent analog signal is in a form of response current.

16. The method of claim 15, further comprising converting the time-dependent analog signal to a time-dependent output voltage prior to converting to the set of digital signals.

17. The method of claim 14, wherein further comprising establishing a time-dependent discharge curve in accordance with the set of digital signals collected during the sampling period.

18. The method of claim 17, wherein the content of the specific component is determined in accordance with the time-dependent discharge curve and a mapping table of peak value versus content of the specific component, the peak value representing a maximum value of the time-dependent discharge curve.

19. The method of claim 17, wherein the content of the specific component is determined in accordance with the time-dependent discharge curve and a mapping table of rising time versus content of the specific component, the rising time corresponding to a maximum value of the time-dependent discharge curve.

20. The method of claim 16, wherein further comprising establishing a voltage-time discharge curve in accordance with the sets of digital signals collected during the sampling period.

* * * * *

UNITED STATES PATENT AND TRADEMARK OFFICE
CERTIFICATE OF CORRECTION

PATENT NO. : 7,454,296 B2 Page 1 of 1
APPLICATION NO. : 10/722549
DATED : November 18, 2008
INVENTOR(S) : Wang et al.

It is certified that error appears in the above-identified patent and that said Letters Patent is hereby corrected as shown below:

At column 6, line 32, please replace "the sets of" with --the set of--.
At column 8, line 19, please replace "the sets of" with --the set of--.

Signed and Sealed this

Twenty-sixth Day of October, 2010

David J. Kappos
*Director of the United States Patent and Trademark Office*